United States Patent
Vogt

(10) Patent No.: US 9,931,430 B2
(45) Date of Patent: Apr. 3, 2018

(54) ANTIMYCOTIC POLYMERISABLE BONE CEMENT AND A METHOD FOR THE PRODUCTION THEREOF

(71) Applicant: Heraeus Medical Gmbh, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

(21) Appl. No.: 15/016,534

(22) Filed: Feb. 5, 2016

(65) Prior Publication Data

US 2016/0235883 A1 Aug. 18, 2016

(30) Foreign Application Priority Data

Feb. 16, 2015 (DE) .................. 10 2015 102 210

(51) Int. Cl.
| | | |
|---|---|---|
| A61L 24/06 | (2006.01) | |
| A61L 24/04 | (2006.01) | |
| A61L 27/54 | (2006.01) | |
| A61L 24/00 | (2006.01) | |
| A61K 31/7048 | (2006.01) | |

(52) U.S. Cl.
CPC ........ *A61L 24/043* (2013.01); *A61K 31/7048* (2013.01); *A61L 24/0015* (2013.01); *A61L 24/0073* (2013.01); *A61L 24/06* (2013.01); *A61L 27/54* (2013.01); *A61L 2300/406* (2013.01); *A61L 2300/802* (2013.01); *A61L 2430/02* (2013.01); *A61L 2430/38* (2013.01)

(58) Field of Classification Search
CPC .. A61K 31/7048; A61K 47/32; A61K 9/0024; A61K 9/145; A61L 2300/406; A61L 2300/802; A61L 2430/02; A61L 2430/38; A61L 24/0015; A61L 24/0073; A61L 24/043; A61L 24/06; A61L 27/54
See application file for complete search history.

(56) References Cited

U.S. PATENT DOCUMENTS

| | | | | |
|---|---|---|---|---|
| 6,383,471 | B1 * | 5/2002 | Chen .................. | A61K 9/1075 424/401 |
| 7,867,981 | B2 | 1/2011 | Cleary et al. | |
| 2013/0030058 | A1 * | 1/2013 | Vogt .................. | A61L 27/16 514/772.6 |
| 2015/0190550 | A1 | 7/2015 | Nusko et al. | |

FOREIGN PATENT DOCUMENTS

| | | |
|---|---|---|
| DE | 2417993 C2 | 7/1982 |
| DE | 102009059276 A1 | 6/2011 |
| EP | 0317120 A1 | 5/1989 |
| EP | 0774958 B1 | 1/1999 |
| EP | 2730296 A2 | 5/2014 |
| JP | 2006504716 A | 2/2006 |
| JP | 2010037252 A | 2/2010 |
| WO | 8806450 A1 | 9/1988 |

OTHER PUBLICATIONS

Tiyaboonchai et al. (International Journal of Pharmaceutics. 2007;329:142-149).*
Pohl et al. (Formatex 2011; pp. 61-71).*
English translation of Matsumoto et al. (JP2010037353); 2010, 6 pages.*
Cunningham et al. (Clin Orthop Relat Res. 2012;470:2671-2676) (Year: 2012).*
Silverberg et al. (Clinical Orthopaedics and Related Research 2002;403:228-231) (Year: 2002).*
Goss et al. (The Journal of Arthroplasty 2007;22(6):902-908) (Year: 2007).*
European Search Report for corresponding application EP 16152082.0 dated Jul. 5, 2016.
Database WPI, Week 201016, Thompson Scientific, London, GB; AN 2010-B81401, XP002759229, & JP 2010 037252 A (Medrex KK) Feb. 18, 2010.
Database EPODOC [online] European Patent Office, The Hague, NL; XP002759230, Database Accession No. JP-2008200727-a & JP2010 037252 A (Medorekkusu KK) Feb. 18, 2010.
C. Salerno, et al., "Lipid-based microtubes for topical delivery of Amphotericin B", Colloids and Surfaces B: Biointerfaces, vol. 107, pp. 160-166, Jul. 1, 2013.
D. Silverberg, et al., "In vitro analysis of antifungal impregnated polymethylmethacrylate bone cement", Database Embase [online], Elsevier Science Publishers, Amsterdam, NL, Oct. 1, 2002, XP002759231.
Y.H. Chang, et al., "Liquid antibiotics in bone cement: an effective way to improve the efficiency of antibiotic release in antibiotic loaded bone cement", Bone and Joint Research, vol. 3, No. 8, Aug. 7, 2014.

(Continued)

*Primary Examiner* — Ernst V Arnold
(74) *Attorney, Agent, or Firm* — Norris McLaughlin & Marcus PA

(57) ABSTRACT

The invention describes a bone cement with antimycotic efficacy based on organic polymers, such as polymethylmethacrylate. The bone cement comprises an antimycotic agent, in particular amphotericin B, that is released from the polymerized bone cement in the presence of water or aqueous media, such as body fluids. According to one alternative, the antimycotic agent is present in particulate form and is encapsulated, at least in part, by a mixture of at least one 1-methylamino-1-deoxy sugar alcohol and at least one fatty acid. In addition, a method for the production of a mixture comprising an antimycotic agent, such as amphotericin B particles, and 1-methylamino-1-deoxy sugar alcohol and at least one fatty acid is proposed. Preferably, the antimycotic agent is encapsulated, at least partially, by 1-methylamino-1-deoxy sugar alcohol and at least one fatty acid.

10 Claims, 1 Drawing Sheet

(56) References Cited

OTHER PUBLICATIONS

Cunningham, B., et al., "Liposomal Formulation Increases Local Delivery of Amphotericin from Bone Cement: A Pilot Study", In: Clin. Orthop. Relat. Res., 2012, vol. 470, S. 2671-2676.
Madigan, S., et al., "Optimisation of the composition of an acrylic bone cement: application to relative amounts of the initiator and the activator/co-initiator in Surgical Simplex (R) P", In: J. Mater. Sci. Mater. Med., 2006, vol. 17, S. 307-311.
German Search Report for corresponding application DE 10 2015 102 210.9 dated Oct. 15, 2015.
Canadian Office Action for corresponding application CA 2918378 dated Mar. 28, 2017.
Translation of Japanese Office Action for corresponding application JP 2016023110 dated Jan. 17, 2017.

\* cited by examiner

ANTIMYCOTIC POLYMERISABLE BONE CEMENT AND A METHOD FOR THE PRODUCTION THEREOF

This application claims foreign priority benefit under 35 U.S.C. § 119 of German Patent Application No. 10 2015 102 210.9, filed Feb. 16, 2015, the disclosures of which patent application is incorporated herein by reference.

The invention describes a bone cement with antimycotic efficacy based on organic polymers, such as polymethylmethacrylate. The bone cement comprises an antimycotic agent, in particular amphotericin B, that is released from the polymerised bone cement in the presence of water or aqueous media, such as body fluids. According to one alternative, the antimycotic agent is present in particulate form and is encapsulated, at least in part, by a mixture of at least one 1-methylamino-1-deoxy sugar alcohol and at least one fatty acid. In addition, a method for the production of a mixture comprising an antimycotic agent, such as amphotericin B particles, and 1-methylamino-1-deoxy sugar alcohol and at least one fatty acid is proposed. Preferably, the antimycotic agent is encapsulated, at least partially, by 1-methylamino-1-deoxy sugar alcohol and at least one fatty acid. The object of the invention is an antimycotic bone cement intended for mechanical anchoring of revision articular endoprostheses in the scope of septic revision surgeries, in which pathogenic microorganisms from the group of fungi, in particular of the yeasts and aspergilli, are the causative agent. In addition, the antibiotic polymethylmethacrylate bone cement is also well-suited for the production of spacers as temporary placeholders in two-stage septic revision surgeries.

Articular endoprostheses are used extensively and very successfully in a broad range of articular diseases aiming to maintain the mobility of the patients. Patients with a weakened immune system, for example in the presence of HIV infections, after organ transplantations and in the presence of cancer diseases, can be subject to the infection of articular endoprostheses by microorganisms from the group of the fungi. These diseases are extremely rare and also very difficult to treat.

In septic revision surgeries, in which bacterial pathogens are the causative agent, one-stage and two-stage replacements of the articular endoprostheses are performed to treat these infections. Revision polymethylmethacrylate bone cements containing an antibiotic or two or more antibiotics have proven expedient for permanent mechanical fixation of the revision articular endoprostheses. Said antibiotics protect the revision articular endoprosthesis and the surrounding bone tissue and soft tissue, at least right after the surgery, from renewed microbial colonisation. Aside from the individualised admixture of antibiotics by the physician, industrially produced revision polymethylmethacrylate bone cements have proven expedient.
Exihibit A In those rare cases, in which fungi are the causative agent of an infection of articular endoprostheses, there is not yet an industrially produced, homogeneous revision polymethylmethacrylate bone cement available, in which effective amounts of an antimycotic agent are released upon exposure to body fluids, such as exudate and blood. For this reason, antimycotic agents that are common in clinical applications have been admixed to normal polymethylmethacrylate bone cement powder thus far. One associated problem is that the majority of the common antimycotic agents, for example of the triazole antimycotic agents, is very poorly soluble in water and shows high protein binding in the human body. For this reason, dissolution of common antimycotic agents from hydrophobic polymethylmethacrylate bone cement is a difficult and it is questionable whether or not amounts of the agent that have an antimycotic efficacy are indeed released.

The antimycotic agent, amphotericin B (CAS 1397-89-3), is a polyene-macrolactone that has been isolated from the streptomyces strain, Streptomyces nodosum. It binds to the steroid, ergosterine, that is typical of fungi and is an ingredient of the fungal cell membrane. The fungicidal effect of amphotericin B has been related to an increase in the permeability of cell membranes for potassium ions (M. Baginski, J. Czub: Amphotericin B and Its New Derivatives—Mode of Action. Current Drug Metabolism 10 (5) (2009) 459-69.). It is particularly advantageous that amphotericin B has a very broad antimycotic efficacy against a wide range of fungi that are pathogenic to man, including of Candida species'. Amphotericin B is only poorly soluble in water in the pH range of 6 to 7. Therefore, for systemic use of amphotericin B in the human body, attempts have been made to produce a preparation that is at least partially soluble in water. Amphotericin B emulsions with lipids have been developed for this purpose (EP0317120). Moreover, adducts with disodium deoxycholate (Barner et al., Antibiotics Annual 1957-1958: 53-58.) and with sodium cholesterylsulfate (EP0303683) are known. These emulsions and adducts are produced using amphotericin B that is dissolved in water or organic solvents. These solvent-dependent processes are very material- and time-consuming.

DE133016A1 discloses a method for the production of a tricalcium phosphate bone ceramic material for use as bone implant, whereby the ceramic material is treated, after the firing process, with a solution containing an agent and is then dried. EP 0642363B1 discloses a hydrogel-coated orthopaedic fastening device, whereby the hydrogel is impregnated with a pharmaceutical agent. The hydrogel expands in the presence of water. It is a disadvantage of the two latter applications that the agent can be impregnated only onto pre-made ceramic implants and also only superficially on the implant.

It was one object of the invention to develop a bone cement with antimycotic efficacy based on organic polymers and monomers, such as polymethylmethacrylate bone cement. The object further consisted of an antimycotically effective amount of the antimycotic agent, preferably amphotericin B, being released from the polymerised bone cement upon exposure to aqueous liquids. Furthermore, it was an object to adapt the water solubility of the antimycotic agent to the purposes specified above without changing its structure. Moreover, the additives used to increase the water suitability shall be inexpensive. Moreover, a simple and inexpensive method is to be developed, in which the antimycotic agent, preferably amphotericin B, can be modified by at least one additive without involving the use of further contaminations, such as solvents, in order to improve its solubility in water.

The objects of the invention are met according to the bone cement, the method, the kit and the use thereof, as described hereinbelow. Advantageous embodiments are presented and illustrated, in detail, in the description.

The object of the invention is an antimycotic polymethylmethacrylate bone cement that comprises methylmethacrylate, at least one polymethylmethacrylate or a polymethylmethacrylate-copolymer, at least one radical initiator, at least one accelerator, and at least one radiopaquer, whereby, in an alternative, the components can be present in a powdered component and a liquid monomer component or in two components that are pasty at room temperature. According to the invention, the bone cement comprises particles containing amphotericin B, whereby the amphotericin B is encapsulated, at least in part, by a mixture of at least one 1-methylamino-1-deoxy sugar alcohol and at least one fatty acid.

It has been found, surprisingly, that a polymethylmethacrylate bone cement that contains amphotericin B, in particular amphotericin B particles that are encapsulated fully or partly by a mixture of a 1-methylamino-1-deoxy sugar alcohol and a fatty acid, releases antimycotically-effective amounts of amphotericin B in the presence of aqueous solutions.

The object of the invention is a polymerisable bone cement, comprising
(i) at least one monomer for radical polymerisation, in particular a liquid monomer;
(ii) at least one organic polymer that is soluble in (i), in particular at least one polymethacrylate or one polymethacrylate-copolymer; and
(ii) at least one polymerisation initiator and at least one antimycotic agent;
(iv) optionally at least one radiopaquer; and
(v) at least one polymerisation accelerator, whereby the antimycotic agent, preferably amphotericin B, is present in a mixture with at least one amino functionalized solubilising agent and at least one carbonic acid.

The bone cement according to the invention is advantageous in that the antimycotic agent is present such as to be distributed both in the matrix of the polymerisable bone cement and in the matrix of the cured bone cement, preferably is distributed approximately homogeneously. It is an essential advantage of the bone cement according to the invention that it is provided in the form of a processable bone cement that is being polymerised after application or can be processed into surgical implants or parts thereof.

According to a particularly preferred embodiment, the bone cement can be present as a 2K system. In 2K systems, the bone cement can be present as paste/paste, as powder/paste and/or powder/liquid components. The two components are mixed with each other for producing the polymerisable bone cement and can be processed. The bone cement according to the invention can be used in simple and economical manner to open any application field of the bone cement to antimycotic applications as well.

Therefore, according to a particularly preferred embodiment, an object of the invention is a bone cement comprising two components, in particular components that are present separated from each other, preferably components A and B, whereby
(i) component A is present as a paste and comprises (a1) at least one monomer for radical polymerisation, (a2) at least one organic polymer that is soluble in (a1), and (a3) at least one polymerisation initiator; and
component B is present as a paste and comprises (b1) at least one monomer for radical polymerisation, (b2) at least one organic polymer that is soluble in (i), (b1), and (b3) at least one polymerisation accelerator; or
(ii) component A is present as a powder and comprises (a1) at least one powdered polyacrylate, (a2) at least one powdered radiopaquer; and (a3) at least one polymerisation initiator; and
component B is present as a liquid or paste and comprises (b1) at least one monomer for radical polymerisation; (b2) optionally, at least one organic polymer that is soluble in (ii), (a1); and (b3) at least one polymerisation accelerator; and whereby at least component A and/or component B comprise(s), as (a4) and/or (b4), at least one antimycotic agent, in particular one antimycotic agent with at least two solubilising agent(s), comprising an amino functionalized solubilizing agent and a carbonic acid.

It is particularly preferred in this context that the antimycotic agent and the solubilising agents are present as a particulate mixture. Without aiming to be limited by theoretical considerations, it is being presumed that the solubilising agents encapsulate the antimycotic agent. Particularly preferably, the solubilising agents are selected from amino-functional polysaccharides, amino-functional polyols, amino-functional polyethers and/or derivatives thereof, as well as carboxylic acids. Preferably, hydrophilic amino-functional solubilising agents and lipophilic carboxylic acids are used together as solubilising agents in a mixture of solubilising agents.

The two solubilising agents preferably form an acid-base adduct that is soluble in aqueous solutions, in particular body fluids.

Moreover, it is presumed, without aiming to be limited by theoretical considerations, that the solubilising agents are capable of encapsulating or embedding the antimycotic agent, in particular amphotericin B, whereby preferably a kind of masking and/or complexing of the poorly water-soluble antimycotic agent takes place.

The agent, amphotericin B, has CAS no. 1397-89-3 and is also referred to as 3-(4-amino-3,5-dihydroxy-6-methyloxan-2-yl)oxy-19,25,27,30,31,33,35,37-octahydroxy-18,20, 21-trimethyl-23-oxo-22,39-dioxabicyclo[33.3.1]nonatriaconta-4,6,8,10,12,14,16-heptaen-38-carboxylic acid.

The purpose of the solubilising agents is to transfer antimycotic agent that is poorly soluble in aqueous media into the aqueous phase. It has been evident that a mixture of at least two solubilising agents, comprising a hydrophilic amino-functional solubilising agents and a hydrophilic alkyl- and/or aryl-functional carboxylic acid as second solubilising agent, can release the antimycotic agent from the polymerised bone cements particularly well in the presence of aqueous media. Moreover, said mixture comprising antimycotic agent and solubilising agents can be dispersed homogeneously in the non-cured bone cement. It is another advantage that the mixture can be produced without the need to have a solvent.

Moreover, it is preferred to have the antimycotic agent be present in a mixture with at least one amino-functional solubilising agent, in particular a hydrophilic amino-functional solubilising agent. In this context, the solubilising agent can comprise amino-functional polysaccharides, N-alkyl- or N-acetyl-functional derivatives of amino-functional polysaccharides, in particular chitosan, amino-deoxy sugars, amino-deoxy sugar alcohols, 1-methylamino-1-deoxy sugar, 1-methylamino-1-deoxy sugar alcohol, such as N-methyl-glucamine, 2-deoxy-2-amino sugar, 2-deoxy-2-amino sugar alcohols, glycosylamine, aminocholesterol, such as 3-aminocholesterol or alkyl- or acetyl derivatives thereof; N-alkyl- or N-acetyl-subsituted aminocholesterol and/or (aminopolyether) α-aminopolyether, α,ω-aminopolyether, as well as derivatives of the solubilising agents specified above. N-alkyl-polyols, N-acetylpolyols, N-alkyl-polyethers, N-acetylpolyethers are also preferred. N-Alkyl-amino sugars, N-Acetyl-amino sugars, N-Alkyl-amino sugars alcohols, N-acetyl-amino sugar alcohols (non-cyclic polyols) are parrticularly preferred, and 1-deoxy-1-methyl-amino sugars, 1-deoxy-1-methylaminosorbit (N-methyl-D-glucamine), 2-deoxy-2-amino sugars, 2-deoxy-2-amino-D-galactose and N-alkyl-functional 2-deoxy-2-amino sugars, N-acetyl-functional 2-deoxy-2-amino sugars, N-alkyl-functional D-glucosamine, N-alkyl-galactosamine, N-acetyl-functional D-glucosamine, N-alkyl-galactosam are likewise preferred.

According to the invention, N-methyl-D-glucamine (1-deoxy-1-methylaminosorbit, CAS 6284-40-8) is preferred as 1-methylamino-1-deoxy sugar alcohol. Any aldoses that can be converted with methylamine at carbon atom 1 and can subsequently be hydrogenated are conceivable for the production of 1-methylamino-1-deoxy sugar alcohols. Allose, altrose, mannose, gulose, idose, galactose, talose, ribose, arabinose, xylose, lyxose, erythrose, and threose are preferred as aldoses in this context. Aside from this, it is feasible, on principle, to use the hydrogenated conversion products of ketoses and methylamine.

Moreover, it is preferred to have the antimycotic agent be present in a mixture with at least one carboxylic acid as solubilising agent, in particular a lipophilic carboxylic acid. The solubilising agent preferably comprises carboxylic acids having alkyl and/or aryl residues, whereby the carboxylic acid comprises at least 8 C-atoms and preferably has an even number of C-atoms. In this context, 8 to 50 C-atoms are particularly preferred, preferably 8 to 24 C-atoms, also preferred are alkan-mono-carboxylic acids, with saturated fatty acids being particularly preferred. Particularly preferred carboxylic acids to be specified here include palmitic acid, lauric acid, myristic acid, stearic acid, nonanoic acid, decanoic acid, undecanoic acid, tridecanoic acid, pentadecanoic acid, heptadecanoic acid, octadecanoic acid, nonadecanoic acid, eicosanoic/icosanoic acid, heneicosanoic acid, docosanoic acid, tetracosanoic acid, hexacosanoic acid, without the carboxylic acids being limited to the ones specified above. Aryl-functional carboxylic acids, such as benzoic acid, phenylacetic acid or other pharmacological carboxylic acids, can just as well be used as solubilising agent.

Saturated fatty acids having an even number of carbon atoms are preferred because they are subject to biological degradation, whereby stearic acid, palmitic acid, myristic acid, and lauric acid are particularly preferred. In addition, it is also feasible to use other fatty acids that can be melted or are liquid at room temperature provided said fatty acids form a solid with the amino-functional solubilising agent.

According to the invention, it is particularly preferred that the antimycotic agent is amphotericin B and is present in a mixture with solubilising agents comprising at least one amino-functional polysaccharide, amino-cholesterol, amino-polyether or derivatives thereof, and at least one carboxylic acid. Preferably, the antimycotic agent, preferably amphotericin B, is encapsulated by a 1-methylamino-1-deoxy sugar alcohol and at least one fatty acid, whereby amphotericin B encapsulated by N-methyl-D-glucamine and at least one fatty acid is particularly preferred.

Particularly preferred weight ratios of antimycotic agent, in particular amphotericin B, to fatty acid and to 1-methyl-amino-1-deoxy sugar alcohol have proven to be from 1.0 to 1.0 up to 1.5 to 1.0 to 6.0 to 6.0, whereby the weight ratio of amphotericin B to fatty acid to 1-methylamino-1-deoxy-sugar alcohol preferably is 1.0 to 1.7 to 1.7.

Moreover, it can be preferred that the antimycotic agent is amphotericin B and that it is present in a mixture of solubilising agents comprising at least one amino-functional polysaccharide, amino-cholesterol, amino-polyether or derivatives thereof, and at least one carboxylic acid, whereby the weight ratio of amino-functional solubilising agent and carboxylic acids is from 1.5 to 1.0 up to 1.0 to 1.0. Alternatively, the molar ratio of amino-functional solubilising agent and carboxylic acid is from 1.5 to 1.0 up to 1.0 to 1.0, particularly preferably 1.0 to 1.7 to 1.7.

Moreover, it is preferred that the weight ratio of antimycotic agent, in particular of amphotericin B, to amino-functional solubilising agent and carboxylic acids is from 1.0 to 1.5 to 1.0 up to 1.0 to 6.0 to 6.0, in particular approximately 1.0 to 1.7 to 1.7. According to an alternative, the molar ratio of the antimycotic agent, in particular of amphotericin B, to amino-functional solubilising agent and carboxylic acids is from 1.0 to 1.5 to 1.0 up to 1.0 to 6.0 to 6.0, whereby a ratio of approximately 1.0 to 1.7 to 1.7 is particularly preferred. In this context, both the weight ratio and the molar ratio can each deviate by +/−0.25 to +/−0.5.

Another subject matter of the invention is a method for the production of an intermediate product for production of the polymerisable bone cement, as well as the intermediate product that can be obtained according to said method, by mixing at least one or two solubilising agent(s) comprising an amino functionalized solubilizing agent and a carbonic acid or a mixture of solubilising agents comprising an amino functionalized solubilizing agent and a carbonic acid and an antimycotic agent. In this context, it is particularly preferred to have the mixing proceed in the absence of a solvent or without any further additions. Preferably, a particulate intermediate product can be obtained according to said method. The particle size of the intermediate product preferably is in the range of equal to 250 µm, in particular of 100 nm to 250 µm, preferably of 50 to 250 µm.

Accordingly, another object of the invention is an intermediate product, in particular a particulate intermediate product, comprising at least one amino-functional solubilising agent and at least one carboxylic acid having alkyl and/or aryl residues, whereby the carboxylic acid comprises at least 8 C-atoms, and, optionally, preferably comprising an antimycotic agent.

According to particularly preferred alternatives, the method is performed (i) by melting at least one or two solubilising agent(s) or a mixture of solubilising agents and adding an antimycotic agent to the melted mixture, or (ii) by using the action of mechanical energy a) to mix, in particular to tribo-chemically grind, at least one or two solubilising agent(s) or a mixture of solubilising agents and an antimycotic agent. Preferably, the amino functional solubilising agents and the carboxylic acid form supra-molecular structures. According to another alternative b), at least two solubilising agents and, optionally, an antimycotic agent can be mixed in a first step b.1), or b.2) a mixture of solubilising agents and an antimycotic agent can be mixed, in particular can be tribo-chemically ground. Preferably, the amino functional solubilising agent and the carboxylic acid for supra-molecular structures, whereby the antimycotic agent is subsequently being mixed with the mixture from b.1) through the action of mechanical energy.

The preparation of the mixture can proceed in any order although it is preferred to first mix the solubilising agents with each other and to then add the antimycotic agent to said mixture, and to mix the mixture again.

The method according to the invention is a particularly environment-friendly method since it fully forgoes the use of solvents. Moreover, the method according to the invention is particularly economical. The mixture obtained, if it is a melt, is cooled and disintegrated. The disintegration can proceed mechanically, for example through grinding, shredding, cutting, etc. Likewise, either the warm melt or the cooled-down melt can be extruded. Subsequently, the mixture is incorporated into a conventional composition of a polymerisable bone cement.

The polymerisable bone cement thus produced, in particular the polymerisable bone cement obtainable according to the method, is physiologically tolerable due to the specific selection of solubilising agents and enables the later release, in particular a delayed release, of the antimycotic agent from the then polymerised bone cement.

The solubilising agent used in the method preferably comprises at least one amino-functional solubilising agent and at least one carboxylic acid having alkyl and/or aryl residues, whereby the carboxylic acid comprises at least 8 C-atoms. According to a particularly preferred variant of the method, the production is effected by (i) a) melting at least one amino-functional solubilising agent and/or at least one carboxylic acid having alkyl and/or aryl residues, whereby the carboxylic acid comprises at least 8 C-atoms, and adding amphotericin B as antimycotic agent to the melted mixture. In subsequent steps, the melt obtained is cooled down and the solidified melt is disintegrated or, alternatively, the malleable melt is being extruded. Alternatively, b) the melted mixture comprising amphotericin B can be cooled down and, optionally, be disintegrated and/or ground through the action of mechanical energy.

According to a further preferred alternative, the mixture can be produced through the action of mechanical energy, such as a tribo-chemical treatment. This can be implemented, for example, by producing the mixture in a ball mill. A Pulverisette 7 made by Fritsch is a preferred ball mill.

Accordingly, the intermediate product can be produced by (ii) the action of mechanical energy by
  a) mixing at least one amino-functional solubilising agent and at least one carboxylic acid having alkyl and/or aryl residues, whereby the carboxylic acid comprises at least 8 C-atoms,
  adding amphotericin B to the mixture obtained and mixing through the action of mechanical energy, or
  b) mixing at least one amino-functional solubilising agent, at least one carboxylic acid having alkyl and/or aryl residues, whereby the carboxylic acid comprises at least 8 C-atoms, and amphotericin B, or
  c) mixing at least one amino-functional solubilising agent or at least one carboxylic acid having alkyl and/or aryl residues, whereby the carboxylic acid comprises at least 8 C-atoms, with amphotericin B, whereby the solubilising agent not added in the first step is subsequently added to the mixture, and subsequently mixing again.

Accordingly, another subject matter of the invention is a method for the production of particles comprising amphotericin B and -1-methylamino-1-deoxy sugar alcohol and a fatty acid.

The method according to the invention can just as well be implemented as follows: Melting the 1-methylamino-1-deoxy sugar alcohol at a temperature above 100° C. Adding at least one fatty acid to the melt at a temperature above 100° C. and, optionally, mixing. Adding the antimycotic agent, in particular amphotericin B, to the melt thus obtained and, optionally, mixing. Cooling down the melt thus obtained, preferably to room temperature.

Grinding the cooled-down melt, which is solidified, at room temperature to form particles with a sieved fraction of less than or equal to 250 µm.

In the step of adding and mixing the antimycotic agent, it is important to cool down the melt to room temperature as close as possible to immediately after mixing with the antimycotic agent, in particular with amphotericin B, such that the thermal stress on the amphotericin B lasts for a few seconds to minutes only. The particular advantage of the method according to the invention is that at least partially encapsulated amphotericin B particles can be produced in a short time, with little effort, and without the use of solvent. The cooling can just as well be effected by introducing or extruding the melt into liquid nitrogen.

Another subject matter of the invention is a composition for use for treatment and/or prevention of mycoses, whereby the composition comprises
  (i) at least one monomer for radical polymerisation, in particular liquid monomer;
  (ii) at least one organic polymer that is soluble in (i), in particular at least one polymethacrylate, or a polymethacrylate-copolymer; and
  (iii) at least one polymerisation initiator; and at least one antimycotic agent; and, optionally,
  (iv) at least one radiopaquer;
  (v) at least one polymerisation accelerator, whereby the antimycotic agent is present in a mixture with at least one or two solubilising agents, comprising an amino functionalized solubilising agent and a carbonic acid.

Another subject matter of the invention is a kit for the production of polymerisable bone cement comprising two components A and B that are present separate from each other. Accordingly, a subject matter of the invention is a kit comprising components A and B, whereby
  (i) component A is present as a paste and comprises (a1) at least one monomer for radical polymerisation, (a2) at least one organic polymer that is soluble in (a1), and (a3) at least one polymerisation initiator; and
  component B is present as a paste and comprises (b1) at least one monomer for radical polymerisation, (b2) at least one organic polymer that is soluble in (i), (b1), and (b3) at least one polymerisation accelerator; or
  (ii) component A is present as a powder and comprises (a1) at least one powdered polyacrylate, (a2) at least one powdered radiopaquer; and (a3) at least one polymerisation initiator; and
  component B is present as a liquid or paste and comprises (b1) at least one monomer for radical polymerisation; (b2) optionally, at least one organic polymer that is soluble in (ii), (a1); and (b3) at least one polymerisation accelerator; and whereby at least component A and/or component B comprise(s), as (a4) and/or (b4), at least one antimycotic agent, in particular one antimycotic agent with at least one solubilising agent, in particular amino-functional, preferably an amino-functional polyol and/or an amino-functional polyether as solubilising agent.

According to a preferred embodiment, a bone cement or kit is provided comprising the following component, whereby
  (i) component A is present as a paste and comprises
  (a1) at least one monomer for radical polymerisation, in particular 15 to 85% by weight, preferably 22 to 70% by weight, more preferably 25 to 60% by weight, particularly preferably 25 to 50% by weight thereof;
  (a2) at least one organic polymer that is soluble in (a1), in particular 5 to 50% by weight, preferably 10 to 40% by weight, particularly preferably 20 to 30% by weight thereof; and
  (a3) at least one polymerisation initiator, in particular 0.01 to 10% by weight, preferably 0.01 to 8% by weight, particularly preferably 0.01 to 5% by weight thereof; and component B is present as a paste and comprises
(b1) at least one monomer for radical polymerisation, in particular 15 to 85% by weight, preferably 20 to 70% by weight, more preferably 25 to 60% by weight, particularly preferably 25 to 50% by weight thereof;
(b2) at least one organic polymer that is soluble in (i), (b1), in particular 5 to 50% by weight, preferably 10 to 40% by weight, particularly preferably 20 to 30% by weight thereof; and
(b3) at least one polymerisation accelerator, in particular 0.0005 to 0.5% by weight thereof; or
(ii) component A is present as a powder and comprises
(a1) at least one powdered polyacrylate, in particular 1 to 95% by weight, preferably 15 to 85% by weight thereof;
(a2) at least one powdered radiopaquer, in particular 3 to 60% by weight, preferably 3 to 30% by weight thereof; and
(a3) at least one polymerisation initiator, in particular 0.01 to 10% by weight, preferably 0.01 to 8% by weight, particularly preferably 0.01 to 5% by weight thereof; and
component B is present as liquid or paste and comprises
(b1) at least one monomer for radical polymerisation, in particular 15 to 85% by weight, preferably 20 to 70% by weight, more preferably 25 to 60% by weight, particularly preferably 25 to 50% by weight thereof;
(b2) optionally, at least one organic polymer that is soluble in (ii), (a1), in particular 5 to 50 by weight, preferably 10 to 40% by weight, particularly preferably 20 to 30% by weight thereof; and
(b3) at least one polymerisation accelerator, in particular 0.0005 to 0.5% by weight thereof; and
whereby at least component A and/or component B comprise (s), as (a4) and/or (b4), at least one antimycotic agent, in particular one antimycotic agent with at least two solubilising agents comprising an amino functionalized solubilising agent and a carbonic acid.

Preferably, 0.01 to 2.0% by weight, in particular 0.01% by weight to 1.0% by weight, preferably 0.05 to 0.5% by weight of components (a4) and/or (b4) are present in the perspective component, such as powder component A or paste A and/or B. In this context, it is preferred to have the antimycotic agent be present in both pastes. The content of antimycotic agent in the total composition of the bone cement preferably is in the range of 0.001 to 2.0% by weight, preferably of 0.001 to 1.0% by weight, particularly preferably in the range of 0.05 to 0.5% by weight.

Whereby it is preferred to mix powder component A and liquid A or paste A at a ratio of approximately 2 to 1 up to 1 to 2. As a matter of rule, pastes A and B can be mixed with each other at any arbitrary ratio, whereby the use of pastes A and B at a ratio of essentially 1 to 1 has proven to be preferred for producing a mixture, whereby the ratio can vary by plus/minus 50% independent of each other.

Another subject matter of the invention is a polymerisable and/or curable bone cement that can be obtained by mixing components A and B. Another subject matter of the invention is a polymerised and/or cured bone cement for treatment and/or prevention of mycoses, whereby the antimycotic agent is released in the presence of moisture, water, aqueous milieu, such as body fluids, or an aqueous solution, in particular with the antimycotic agent being released in delayed manner. Yet another subject matter of the invention is a form body that can be obtained by forming on polymerising the curable (synonymous to polymerisable) bone cement Another subject matter of the invention according to another embodiment is a surgical implant or part of an implant, antimycotic implant, revision implant, screw, nail, surgical plate, for mechanical fixation of primary total articular endoprostheses, for mechanical fixation of revision total articular endoprostheses, for augmentation of osteoporotic bone tissue and, particularly preferably, for vertebroplasty, kyphoplasty, and augmentation of drill holes in osteoporotic bone tissue, for filling bone cavities, for femuroplasty, for the manufacture of spacers, for mechanical fixation of articular endoprostheses, for coverage of skull defects or for production of carrier materials for local antibiotics therapy or as carrier material for local release of pharmaceutically active substances.

According to an embodiment, a subject matter of the invention is a bone cement comprising, as monomer, at least one alkyl-2-acrylic acid alkylester, aryl-2-acrylic acid alkylester, arylalkyl-2-acrylic acid alkylester, each independently having 1 to 20 C-atoms in the alkyl group, each independently having 6 to 14 C-atoms in the aryl group, each independently having 6 to 14 C-atoms in the arylalkyl group, and each independently having 1 to 10 C-atoms in the alkylester group, or a mixture comprising at least two of said monomers.

Preferably, the paste according to the invention contains an amount of the monomer for radical polymerisation in the range of 15 to 85% by weight, more preferably 20 to 70% by weight, even more preferably 25 to 60% by weight, and particularly preferably 25 to 50% by weight, each relative to the total weight of the paste according to the invention.

The organic polymer is preferably selected from at least one poly(alkyl-2-acrylic acid alkylester), poly(aryl-2-acrylic acid alkylester), poly(arylalkyl-2-acrylic acid alkylester), each independently having 1 to 20 C-atoms in the alkyl group, each independently having 6 to 14 C-atoms in the aryl group, each independently having 6 to 14 C-atoms in the arylalkyl group, and each independently having 1 to 10 C-atoms in the alkylester group, or a mixture comprising at least two of said polymers. Preferably, the organic polymer is selected from the group of poly(methacrylic acid methylester), poly(methacrylic acid ethylester), poly(methylmethacrylic acid propylester), poly(methacrylic acid isopropylester), poly(methylmethacrylate-co-methylacrylate), poly(styrene-co-methylmethacrylate), copolymers of said compounds, and a mixture comprising at least two of said polymers.

Another subject matter of the invention is a bone cement comprising at least one organic polymer, such as a poly(methacrylic acid methylester) (PMMA) and methacrylic acid methylester (MMA) as monomer.

A polymer that is soluble in the at least one monomer for radical polymerisation shall be understood to be a polymer of which at least 10 g/l, preferably at least 25 g/l, particularly preferably at least 50 g/l, and even more particularly preferably at least 100 g/l dissolve in said monomer for radical polymerisation. The polymer that is soluble in the polymerisable monomer can be a homopolymer or a copolymer. Said soluble polymer preferably is a polymer with a mean (by weight) molar mass (Mw) of at least 150,000 g/mol, in particular at least 200,000 g/mol and up to more than or equal to 5,000,000 g/mol. The soluble polymer can, for example, be a polymer or copolymer of a methacrylic acid ester. According to a particularly preferred embodiment, the at least one soluble polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), poly (styrene-co-methylmethacrylate), and a mixture of at least two of said polymers.

The amount of the polymer that is soluble in said monomer for radical polymerisation that is present in the bone cement according to the invention usually is in the range of 1 to 85% by weight, relative to the total weight of the bone cement. Accordingly, the organic polymer content of any of the subsequent pastes A, B, and/or liquid B as well as of powder component A can, independent of each other, be 1 to 85% by weight relative to the respective total composition of paste, liquid or powder component.

Polymers, in particular polyacrylates, having a molecular weight (MW) of preferably more than or equal to 200,000 g/mol are used as polymers that are soluble in the monomers for producing powder components, whereby molecular weights of more than or equal to 500,000 g/mol are preferred. Polymers having a molecular weight of less than or equal to 500,000 g/mol can also be used in pastes. In this context, the suitable molecular weight is determined, on the one hand, by whether a paste or a powder component is being produced and by the further components present in the paste, and by the polymer having to be soluble in the monomer that is used.

A bone cement according to the invention comprises, aside from the soluble organic polymer, in particular polymethylmethacrylate (PMMA), and the monomer for radical polymerisation, in particular methacrylic acid methylester, a particulate inorganic additive, preferably at a concentration of 0.01 to 0.5% by weight, in particular of 0.01 to 0.25% by weight, preferably of 0.02 to 0.14% by weight relative to the total composition. According to the invention, the bone cement dough produced by mixing the powder component and the liquid monomer component comprises the particulate inorganic additive at a concentration from 0.02 to 0.14 by weight. In addition to the components mentioned above, a bone cement according to the invention comprises a radiopaquer, a polymerisation initiator and/or a polymerisation accelerator and, optionally, additional filling agents other than the additive that simply possess a thickening effect.

The particulate inorganic additive is selected from the group of pyrogenic silicon dioxide, pyrogenic mixed metal-silicon oxides, bentonite, montmorillonite, and a mixture containing at least two of said additives. Moreover, it is also feasible to use pyrogenic silicon dioxide made hydrophobic. The hydrophobic silicon dioxide can be produced according to the prior art through treating pyrogenic silicon dioxide with dialkyldichlorosilanes (e.g. dimethyldichlorosilane).

The bone cement, pastes, liquid and/or powder components according to the invention can contain at least one polymerisation initiator (which preferably is soluble in the monomer for radical polymerisation), at least one polymerisation accelerator (which preferably is soluble in the monomer for radical polymerisation), at least one polymerisation co-accelerator, if applicable, or at least one polymerisation initiator, at least one polymerisation accelerator, and, if applicable, at least one polymerisation co-accelerator.

In the case of a one-component system being the composition according to the invention, the polymerisation initiator preferably is an activatable polymerisation initiator, e.g. a photoinitiator that is dissolved or suspended in the composition, which is present as a paste, or a photoinitiator system that is dissolved or suspended in the paste. It is feasible just as well to provide an initiator or initiators where it/they are temporarily in contact with the paste, for example in a container part, a dosing facility or a transport cannula.

Moreover, in a one-component system, the bone cement or paste according to the invention can also contain an electrically conductive radiopaquer aside from the activatable polymerisation initiator. Particles made of cobalt, iron, NdFeB, SmCo, cobalt-chromium steel, zirconium, hafnium, titanium, titanium-aluminium-silicon alloys, and titanium-niobium alloys having a particle size of 0.5-500 μm are particularly well-suited in this context. It is feasible to induce eddy currents in said electrically conductive radiopaquer through alternating magnetic fields with a frequency in the range of 500 Hz to 50 kHz which cause the opaquer to heat up. Due to heat transmission, the initiator is heated as well and induced to thermally disintegrate.

Conceivable as polymerisation initiator are, in particular, peroxides and barbituric acid derivatives, whereby preferably at least 1 g/l, more preferably at least 3 g/l, even more preferably at least 5 g/l, and particularly preferably at least 10 g/l of the peroxides and barbituric acid derivatives can dissolve(s) in the polymerisable monomer at a temperature of 25° C.

According to the invention, a peroxide is understood to mean compounds that contain at least one peroxo group (—O—O—). The peroxide preferably comprises no free acid groups. The peroxide can be an inorganic peroxide or an organic peroxide, such as, for example, a toxicologically acceptable hydroperoxide. According to a particularly preferred embodiment, the peroxide is selected from the group consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, and a mixture of at least two thereof. The barbituric acid derivative preferably is a barbituric acid derivative selected from the group consisting of 1-mono-substituted barbiturates, 5-mono-substituted barbiturates, 1,5-di-substituted barbiturates, and 1,3,5-tri-substituted barbiturates. According to a particular refinement of the paste according to the invention, the barbituric acid derivative is selected from the group consisting of 1,5-di-substituted barbiturates and 1,3,5-tri-substituted barbiturates. It is preferred to use 1,5-disubstituted thiobarbiturates or 1,3,5-trisubstituted thiobarbiturates. According to a preferred embodiment, the substituents each have a length of 1 to 10 carbon atoms. According to a particularly preferred embodiment, the barbituric acid derivative is selected from the group consisting of 1-cyclohexyl-5-ethyl-barbituric acid, 1-phenyl-5-ethyl-barbituric acid, and 1,3,5-trimethyl-barbituric acid.

Heavy metal compounds selected from the group consisting of heavy metal salts and heavy metal complexes are preferred as polymerisation accelerator. Heavy metal compounds that are preferred according to the invention are selected from the group consisting of copper(II) hydroxide, copper(II) methacrylate, copper(II) acetylacetonate, copper (II)-2-ethyl-hexanoate, cobalt(II) hydroxide, cobalt(II)-2-ethyl-hexanoate, basic copper(II) carbonate, iron(II)-2-ethyl-hexanoate, iron(III)-2-ethyl-hexanoate, and a mixture of at least two thereof.

According to another embodiment, the bone cement or at least one paste, liquid or powder component can comprise a polymerisation accelerator that is selected from the group consisting of N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, pyromellitic acid diimide, and a mixture of at least two thereof.

Another advantageous refinement of the invention comprises the use, as polymerisation accelerator, of combinations of heavy metal salts and at least one member of the group comprising N,N-dimethyl-p-toluidine, N,N-bis-hydroxyethyl-p-toluidine, N,N-dimethyl-aniline, trioctylmethylammoniumchloride, tetrabutylammoniumchloride, lithium chloride, saccharin, 1,8-diazabicyclo[5.4.0]undec-7-ene, and 1,5-diazabicyclo(4.3.0)non-5-ene, phthalimide, maleimide, succinimide, and pyromellitic acid diimide. In this context, combinations of two and combinations of three different polymerisation accelerators are disclosed in the scope of the invention.

An advantageous refinement of the invention is that the composition according to the invention or any of the pastes A, B or liquid B or powder component A contains at least one co-polymerisation accelerator, if applicable, whereby tertiary amines and amidines are preferred as polymerisation co-accelerators, and whereby N,N-dimethyl-p-toluidine, N,N-bis-hydroxyethyl-p-toluidine, N,N-dimethyl-aniline, 1,8-diazabicyclo[5.4.0-]undec-7-ene, and 1,5-diazabicyclo (4.3.0)-non-5-ene are particularly preferred as co-accelerators.

The bone cement according to the invention, in particular in the form of a paste, can contain a (total) amount of the polymerisation initiator, polymerisation accelerator, polymerisation co-accelerator or the polymerisation initiator, polymerisation accelerator, and polymerisation co-accelerator of up to 10% by weight, relative to the total weight of the bone cement or, each independent of each other, relative to the total weight of any of the pastes A, B liquid B or powder component A.

The bone cement according to the invention, in particular in the form of a paste, or pastes A, B or liquid B or powder component A, can contain further ingredients aside from the components mentioned above.

According to a preferred embodiment of the bone cement according to the invention or of any of the pastes A, B, liquid B or powder component A, these can, each independent of each other, contain at least one radiopaquer. The radiopaquer can be a common radiopaquer in this field. Suitable radiopaquers can be soluble or insoluble in the monomer for radical polymerisation. The radiopaquer is preferably selected from the group consisting of metal oxides (such as, for example, zirconium dioxide), barium sulfate, toxicologically acceptable heavy metal particles (such as, for example, tantalum), ferrite, magnetite (supramagnetic magnetite also, if applicable), and biocompatible calcium salts. Said radiopaquers preferably have a mean particle diameter in the range of 10 nm to 500 μm. Moreover, conceivable radiopaquers also include esters of 3,5-bis(acetamido)-2,4,6-triiodobenzoic acid, gadolinium compounds, such as gadolinium chelate involving the esters of 1,4,7,10-tetraazacyclododecan-1,4,7, 10-tetraacetic acid (DOTA). The radiopaquer concentrations, in particular the zirconium dioxide concentration, in the bone cement or any of the pastes A, B, liquid B or powder component A can, each independent of each other, be in the range of, for example, 3 to 30% by weight relative to the corresponding total composition. Radiopaquers are not considered to be filling agents herein.

According to a further preferred embodiment, the bone cement according to the invention or at least one of pastes A, B, liquid B or powder component A can contain at least one stabiliser. The stabiliser should be suitable to prevent spontaneous polymerisation of the monomers for radical polymerisation that are contained in the paste. Moreover, the stabiliser should not undergo interfering interactions with the other ingredients contained in the paste according to the invention. Stabilisers of said type are known according to the prior art. According to a preferred embodiment, the stabiliser is 2,6-di-tert-butyl-4-methylphenol and/or 2,6-di-tert-butyl-phenol.

The invention is illustrated through the examples presented in the following, though without limiting the scope of the invention to said examples.

EXEMPLARY EMBODIMENTS

Preparation of Encapsulated Amphotericin B Particles

Particles for Example 1

A total of 2.000 g N-methylglucamine were weighed into a round-edge flask. The N-methylglucamine was melted while stirring at a temperature of 140° C. After all of the N-methylglucamine was melted, 2.000 g palmitic acid were added and stirring at 140° C. was continued for 10 minutes. Then, 0.400 g amphotericin were added while stirring until the amphotericin B particles were fully dispersed in the melt Then, the sample was immediately cooled to room temperature. The melt solidified in the process. Then the melt was ground into a powder using a mortar.

Particles for Example 2

A total of 1.000 g N-methylglucamine were weighed into a round-edge flask. The N-methylglucamine was melted while stirring at a temperature of 140° C. After all of the N-methylglucamine was melted, 1.000 g palmitic acid were added and stirring at 140° C. was continued for 10 minutes. Then, 0.400 g amphotericin were added while stirring until the amphotericin B particles were fully dispersed in the melt Then, the sample was immediately cooled to room temperature. The melt solidified in the process. Then the melt was ground into a powder using a mortar.

Particles for Example 3

A total of 0.700 g N-methylglucamine were weighed into a round-edge flask. The N-methylglucamine was melted while stirring at a temperature of 140° C. After all of the N-methylglucamine was melted, 0.700 g palmitic acid were added and stirring at 140° C. was continued for 10 minutes. Then, 0.400 g amphotericin were added while stirring until the amphotericin B particles were fully dispersed in the melt Then, the sample was immediately cooled to room temperature. The melt solidified in the process. Then the melt was ground into a powder using a mortar.

The amphotericin B particles prepared earlier were then used to produce the cement powder of examples 1-3. The cement powder of example 4 was a control and was composed from Palacos R and pure additive. The cement powder of example 5 consisted of pure Palacos R cement powder.

Composition of the Cement Powders of Example 1-5

| | | Composition of the cement powders | | |
|---|---|---|---|---|
| | | Particles | | |
| Example | Palacos R [g] | Amphotericin B [mg] | 1-N-Methyl-D-glucamine [mg] | Palmitic acid [mg] |
| 1 | 40.0 | 45 | 227 | 227 |
| 2 | 40.0 | 83 | 208 | 208 |

-continued

Composition of the cement powders

| Example | Palacos R [g] | Particles Amphotericin B [mg] | 1-N-Methyl-D-glucamine [mg] | Palmitic acid [mg] |
|---|---|---|---|---|
| 3 | 40.0 | 111 | 194 | 294 |
| 4 | 40.0 | — | 250 | 250 |
| 5 | 40.0 | — | — | — |

For the subsequent production of test bodies, 40.5 g each of the cement powders of examples 1 to 5 were mixed with 20 mL of monomer liquid each. The monomer liquid in each case was composed from 18.50 methylmethacrylate, 0.38 g N,N-dimethyl-p-toluidine, 0.002 g hydroquinone, and traces of chlorophyllin (E241). After mixing the cement powders of examples 1-4 with 20 mL of monomer liquid each, a plastically deformable, greenish cement dough was produced after approx. 60 seconds and was used to produce test bodies. The cement dough was cured after approximately 4 minutes.

Strip-shaped test bodies sized 3.3 mm×10.0 mm×75 mm were produced for the determination of flexural strength and flexural modulus in accordance with ISO 5833. Cylinder-shaped test bodies with a diameter of 6 mm and a height of 10 mm were produced for the determination of the compressive strength. A Zwick Z010 universal testing apparatus was used in the determination of the flexural strength, flexural modulus, and compressive strength in accordance with ISO 5833.

| Example | Flexural strength [MPa] | Flexural modulus [MPa] | Compressive strength [MPa] |
|---|---|---|---|
| 1 | 63.3 ± 1.7 | 2703 ± 70 | 80.9 ± 4.2 |
| 2 | 61.8 ± 1.3 | 2630 ± 122 | 85.5 ± 0.8 |
| 3 | 63.4 ± 0.9 | 2743 ± 84 | 86.5 ± 1.9 |
| 4 | 61.9 ± 1.1 | 2625 ± 50 | 86.6 ± 2.7 |
| 5 | 69.6 ± 1.3 | 2897 ± 117 | 91.9 ± 1.7 |

ISO 5833 requires a flexural strength in excess of 50 MPa, a flexural modulus in excess of 1,800 MPa, and a compressive strength in excess of 70 MPa. The amphotericin B- and additive-modified bone cements of examples 1-3 comply with the requirements of ISO 5833 with regard to flexural strength, flexural modulus, and compressive strength.

For the testing of the antimycotic effect, the cements of examples 1-5 were used to produce cylinder-shaped test bodies with a diameter of 20 mm and a height of 3 mm. The test of the antimycotic effect was performed similar to DIN 58940-3 and Pharm. Eur. chapter 2.7.2. Candida albicans ATCC 10231 was used as the test germ. Three test bodies of each example were tested in parallel for their antimycotic effect.

The yeasts were grown in 2 transfers on caseine peptone-soy flour peptone-agar (TSA) for 40 to 48 hours at 35-37° C. Subsequently, the germs were rinsed off with 5 mL 0.9% NaCl solution and adjusted to approximately $10^6$ cfu/mL through photometric extinction measurements at 575 nm. A total of 100 µl germ suspension each were placed in 20 mL TSA maintained at a temperature of 42-45° C. (TSA, liquid) such that the final concentration was approximately $10^5$ cfu per test. Each test sample was tested in triplicate The plates were incubated for 48 hours at 35-37° C. Subsequently, the corresponding inhibitory zone (=germ-free zone) on the plates was determined in units of millimeters.

| Example | Diameter of inhibitory zone [mm] Test body 1 | Test body 2 | Test body 3 |
|---|---|---|---|
| 1 | 32 | 30 | 32 |
| 2 | 31 | 33 | 32 |
| 3 | 35 | 34 | 35 |
| 4 | — | — | — |
| 5 | — | — | — |

BRIEF DESCRIPTION OF THE DRAWINGS

FIG. 1: Agar plate with test body of example 1
FIG. 2: Agar plate with test body of example 2
FIG. 3: Agar plate with test body of example 3
FIG. 4: Agar plate with test body of example 4
FIG. 5: Agar plate with test body of example 5

Figure 1:
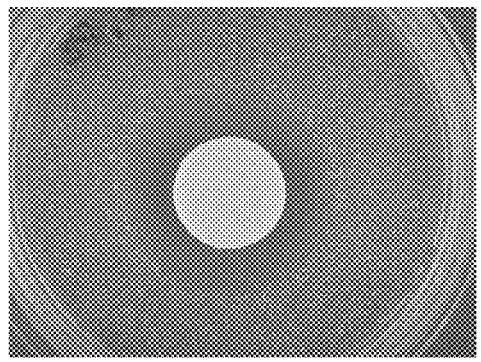
FIGS. 1 to 5 show.
Figure 2:
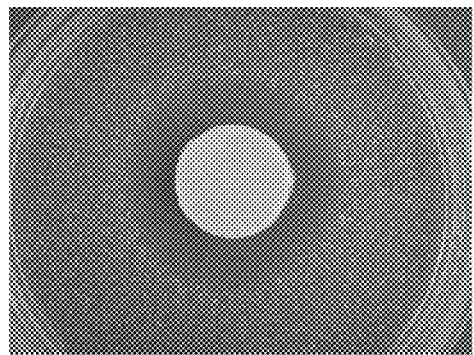
Figure 3:
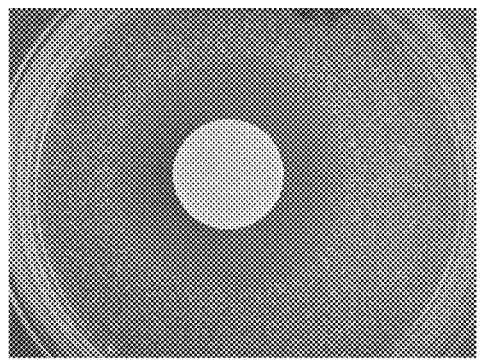
Figure 4:
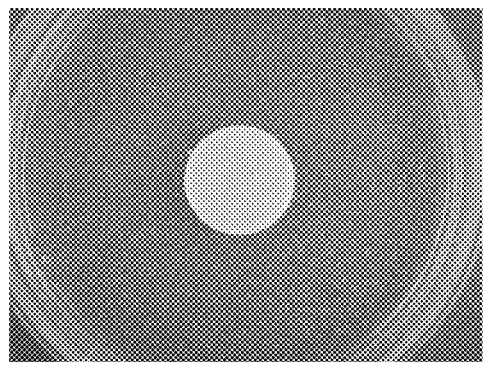
Figure 5:
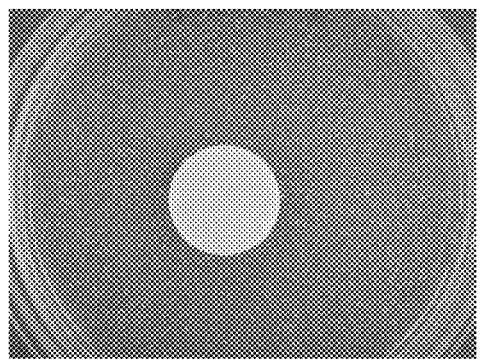

All test bodies of examples 1-3 showed a clearly recognisable inhibitory zone. The test bodies of example 5 showed no inhibition of yeast growth. Obviously, Palacos R cement has no antimycotic effect. Likewise, the test bodies of example 4 showed no inhibitory effect on yeast growth. This means that the combination of Palacos R cement and additive also has no antimycotic effect. The antimycotic effect of the test bodies of examples 1-3 is based on the amphotericin B particles.

In analogy to the amphotericin B particles of examples 1-3, amphotericin B particles were also prepared using the combination of N-methylglucamine and lauric acid, N-methylglucamine and myristic acid, and N-methylglucamine and stearic acid. Said particles showed comparable behaviour in the polymethylmethacrylate bone cement as the particles with the combination of N-methylglucamine and palmitic acid.

The invention claimed is:
1. A polymerizable bone cement, comprising
 (i) at least one monomer for radical polymerization, wherein the monomer (i) is selected from the group consisting of alkyl-2-acrylic acid alkylester, aryl-2-acrylic acid alkylester, and arylalkyl-2-acrylic acid alkylester, each independently having 1 to 20 C-atoms in the alkyl group, each independently having 6 to 14 C-atoms in the aryl group, each independently having 6 to 14 C-atoms in the arylalkyl group, and each independently having 1 to 10 C-atoms in the alkylester group, and a mixture comprising at least two of said monomers; and
 (ii) at least one organic polymer that is soluble in (i); and
 (iii) at least one polymerization initiator; and
 (iv) at least one radiopaquer; and
 (v) at least one antimycotic agent
 wherein
 the at least one antimycotic agent is encapsulated by a 1-methylamino-1-deoxy sugar alcohol and at least one fatty acid.
2. The bone cement according to claim 1, comprising components A and B, wherein:
 (i) component A is present as a paste and comprises
  (a1) at least one monomer for radical polymerization; and
  (a2) at least one organic polymer that is soluble in (a1); and

(a3) at least one polymerization initiator; and
component B is present as a paste and comprises
(b1) at least one monomer for radical polymerization; and
(b2) at least one organic polymer that is soluble in (b1); and
(b3) at least one polymerization accelerator; or
(ii) component A is present as a powder and comprises
(a1) at least one powdered polyacrylate; and
(a2) at least one powdered radiopaquer; and
(a3) at least one polymerization initiator; and
component B is present as a liquid or paste and comprises
(b1) at least one monomer for radical polymerization; and
(b2) at least one organic polymer that is soluble in (b1); and
(b3) at least one polymerization accelerator; and
wherein:
(A) component A further comprise as (a4) at least one antimycotic agent, or at least one antimycotic agent mixed with at least one solubilising agent, or
(B) component B further comprises as (b4) at least one antimycotic agent, or at least one antimycotic agent mixed with at least one solubilizing agent, or
(C) both A and B.

3. The bone cement according to claim 1, wherein the antimycotic agent is amphotericin B.

4. The bone cement according to claim 1, wherein the antimycotic agent is present in a mixture with at least one fatty acid comprising at least 8 C-atoms.

5. The bone cement according to claim 4, wherein the fatty acid is selected from the group consisting of palmitic acid, lauric acid, myristic acid, stearic acid, nonanoic acid, decanoic acid, undecanoic acid, tridecanoic acid, pentadecanoic acid, heptadecanoic acid, octadecanoic acid, nonadecanoic acid, eicosanoic/icosanoic acid, heneicosanoic acid, docosanoic acid, tetracosanoic acid, and hexacosanoic acid.

6. The bone cement according to claim 1, wherein:
the at least one organic polymer (ii) is selected from the group consisting of poly(alkyl-2-acrylic acid alkylester), poly(aryl-2-acrylic acid alkylester), and poly(arylalkyl-2-acrylic acid alkylester), each independently having 1 to 20 C-atoms in the alkyl group, each independently having 6 to 14 C-atoms in the aryl group, each independently having 6 to 14 C-atoms in the arylalkyl group, and each independently having 1 to 10 C-atoms in the alkylester group, or a mixture comprising at least two of said polymers.

7. A kit comprising components A and B, wherein:
(i) component A is present as a paste and comprises
(a1) at least one monomer for radical polymerization wherein the monomer (a1) is selected from the group consisting of alkyl-2-acrylic acid alkylester, aryl-2-acrylic acid alkylester, and arylalkyl-2-acrylic acid alkylester, each independently having 1 to 20 C-atoms in the alkyl group, each independently having 6 to 14 C-atoms in the aryl group, each independently having 6 to 14 C-atoms in the arylalkyl group, and each independently having 1 to 10 C-atoms in the alkylester group, and a mixture comprising at least two of said monomers; and
(a2) at least one organic polymer that is soluble in (a1); and
(a3) at least one polymerization initiator; and
component B is present as a paste and comprises
(b1) at least one monomer for radical polymerization wherein the monomer (b1) is selected from the group consisting of alkyl-2-acrylic acid alkylester, aryl-2-acrylic acid alkylester, and arylalkyl-2-acrylic acid alkylester, each independently having 1 to 20 C-atoms in the alkyl group, each independently having 6 to 14 C-atoms in the aryl group, each independently having 6 to 14 C-atoms in the arylalkyl group, and each independently having 1 to 10 C-atoms in the alkylester group, and a mixture comprising at least two of said monomers; and
(b2) at least one organic polymer that is soluble in (i), (b1); and
(b3) at least one polymerization accelerator; or
(ii) component A is present as a powder and comprises
(a1) at least one powdered polyacrylate; and
(a2) at least one powdered radiopaquer; and
(a3) at least one polymerization initiator; and
component B is present as a liquid or paste and comprises
(b1) at least one monomer for radical polymerization wherein the monomer (b1) is selected from the group consisting of alkyl-2-acrylic acid alkylester, aryl-2-acrylic acid alkylester, and arylalkyl-2-acrylic acid alkylester, each independently having 1 to 20 C-atoms in the alkyl group, each independently having 6 to 14 C-atoms in the aryl group, each independently having 6 to 14 C-atoms in the arylalkyl group, and each independently having 1 to 10 C-atoms in the alkylester group, and a mixture comprising at least two of said monomers; and
(b2) at least one organic polymer that is soluble in (ii), (a1)(b1); and
(b3) at least one polymerization accelerator; and
wherein:
(A) component A comprise as (a4) at least one antimycotic agent and at least two solubilizing agents comprising a 1-methylamino-1-deoxy sugar alcohol and a fatty acid, or
(B) component B comprises as (b4) at least one antimycotic agent and at least two solubilizing agents comprising a 1-methylamino-1-deoxy sugar alcohol and a fatty acid, or
(C) both (A) and (B).

8. A polymerizable bone cement obtained by mixing components A and B according to claim 2.

9. A polymerized, cured bone cement obtainable by mixing components A and B according to claim 2 wherein the antimycotic agent is released in the presence of moisture, water, aqueous milieu, or an aqueous solution.

10. A form body obtained by forming and polymerizing the bone cement according to claim 8.

* * * * *